(12) United States Patent
Ikhlef (10) Patent No.: US 10,314,553 B2
(45) Date of Patent: Jun. 11, 2019

(54) FOCAL SPOT POSITION CONTROL USING PRE-PATIENT COLLIMATOR WITH BEAM TRACKING

(71) Applicant: FMI Medical Systems Co., Ltd., Zhejiang (CN)

(72) Inventor: Abdelaziz Ikhlef, Hudson, OH (US)

(73) Assignee: FMI Medical Systems Co., Ltd., Zhejiang (CN)

( * ) Notice: Subject to any disclaimer, the term of this patent is extended or adjusted under 35 U.S.C. 154(b) by 464 days.

(21) Appl. No.: 15/003,601

(22) Filed: Jan. 21, 2016

(65) Prior Publication Data

US 2017/0209106 A1 Jul. 27, 2017

(51) Int. Cl.
*A61B 6/00* (2006.01)
*A61B 6/03* (2006.01)
*A61B 6/06* (2006.01)
*G21K 1/02* (2006.01)

(52) U.S. Cl.
CPC .............. *A61B 6/06* (2013.01); *A61B 6/032* (2013.01); *A61B 6/4291* (2013.01); *A61B 6/5205* (2013.01); *A61B 6/545* (2013.01); *A61B 6/582* (2013.01); *A61B 6/583* (2013.01); *A61B 6/4021* (2013.01); *G21K 1/02* (2013.01)

(58) Field of Classification Search
CPC .. G21K 1/02; A61B 6/032; A61B 6/06; A61B 6/4021; A61B 6/545; A61B 6/582
See application file for complete search history.

(56) References Cited

U.S. PATENT DOCUMENTS

| | | | |
|---|---|---|---|
| 5,550,886 A * | 8/1996 | Dobbs | A61B 6/032 378/19 |
| 5,644,614 A | 7/1997 | Toth et al. | |
| 6,134,301 A | 10/2000 | Mruzek et al. | |
| 6,137,857 A | 10/2000 | Hoffman et al. | |
| 6,173,039 B1 | 1/2001 | Hampel et al. | |
| 6,298,117 B1 | 10/2001 | Hampel et al. | |
| 7,418,082 B2 | 8/2008 | Levene et al. | |
| 2005/0094762 A1 * | 5/2005 | Dunham | A61B 6/06 378/19 |
| 2012/0087462 A1 | 4/2012 | Ikhlef | |
| 2013/0121475 A1 | 5/2013 | Deych et al. | |
| 2014/0185745 A1 * | 7/2014 | Wang | A61B 6/032 378/16 |
| 2014/0355734 A1 | 12/2014 | Ying | |

* cited by examiner

*Primary Examiner* — Chih-Cheng Kao
(74) *Attorney, Agent, or Firm* — Fishman Stewart PLLC (57) ABSTRACT

A CT scanning system includes a rotatable gantry having an opening for receiving an object to be scanned, an x-ray tube, and a detector comprising an imaging area of pixels and a calibration area of pixels. The system further includes a pre-patient collimator positioned between the x-ray tube and the detector having first and second apertures that pass x-rays respectively to at least a portion of the imaging area of pixels, and to the calibration area of pixels, a motor configured to move the pre-patient collimator, and a computer programmed to determine a focal spot location using energy derived from x-rays that fall upon the calibration area of pixels, and issue commands to a motor to adjust a position of the pre-patient collimator based on the determination.

16 Claims, 5 Drawing Sheets

FOCAL SPOT POSITION CONTROL USING PRE-PATIENT COLLIMATOR WITH BEAM TRACKING

TECHNICAL FIELD

This disclosure relates generally to diagnostic imaging and, more particularly, to an improved pre-patient collimator in computed tomography (CT).

BACKGROUND

Typically, in computed tomography (CT) imaging systems, a rotatable gantry includes an x-ray tube, detector, data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed, and the processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Imaging data may be obtained using x-rays that are generated at a single polychromatic energy. However, some systems may obtain multi-energy images that provide additional information for generating images.

Dose management in CT has become increasingly important in recent years. Thus, in a typical CT scanner, a pre-patient collimator is used to limit x-ray exposure only to the region of interest (ROI) for imaging. To achieve this, collimator apertures made typically of tungsten are included that provided for a different beam width. In general, the pre-patient collimator is used to reduce overbeaming and to control it. Overbeaming is commonly referred to as an amount of the x-ray beam that is incident to the patient which lies outside the active detector area in the Z-axis. Because the focal spot in the Z-axis is not a point, there will typically be overbeaming due to the penumbra from the focal spot. The penumbra refers to the partial outer region that falls outside the umbra, and the umbra typically refers to a full inner region of the x-rays that pass through the patient from the source focal spot.

The penumbra is fixed for x-ray apertures in Z. However, the ratio of overbeaming to the x-ray aperture will decrease with the size of the aperture. Consequently, the dose to the patient will increase when the total beam width decreases. Some manufacturers design the aperture(s) having moving edges or "Z-axis focal spot tracking" to track focal spot umbra and penumbra.

In a design having moving edges, an algorithm tracks focal spot motion and controls position of the aperture through which the x-rays pass. This typically results in complex and expensive hardware to account for the geometric layout of the detector plane with respect to the focal spot, and the distances therebetween. Such a design can improve dose efficiency by maintaining a small aperture without affecting image quality. In such a design, when the focal spot moves in the Z-axis (such as due to mechanical or thermal drift), the aperture is adjusted and aligned to cover only the beam for the desired ROI. Such a design includes sophisticated control of the slit with high precision motors, typically including two or more motors.

Thus, there is a need to improve tracking of the focal spot.

BRIEF DESCRIPTION

Embodiments are directed toward a method of using and apparatus of an improved pre-patient collimator in computed tomography (CT).

According to one aspect, a CT scanning system includes a rotatable gantry having an opening for receiving an object to be scanned, an x-ray tube, and a detector comprising an imaging area of pixels and a calibration area of pixels. The system further includes a pre-patient collimator positioned between the x-ray tube and the detector having first and second apertures that pass x-rays respectively to at least a portion of the imaging area of pixels, and to the calibration area of pixels, a motor configured to move the pre-patient collimator, and a computer programmed to determine a focal spot location using energy derived from x-rays that fall upon the calibration area of pixels, and issue commands to a motor to adjust a position of the pre-patient collimator based on the determination.

According to another aspect, a method of CT imaging includes passing x-rays through an opening in a pre-patient collimator, through an object, and to at least a portion of a detector, the detector including imaging pixels and calibration pixels, determining a focal spot location using energy derived from x-rays that fall upon the calibration area of pixels, and adjusting a position of the pre-patient collimator based on the determination.

Various other features and advantages will be made apparent from the following detailed description and the drawings.

DETAILED DESCRIPTION

The operating environment of disclosed embodiments is described with respect to a sixteen-slice computed tomography (CT) system. Embodiments are described with respect to a "third generation" CT scanner, however it is contemplated that the disclosed embodiments are applicable to other imaging systems as well, and for CT systems having more or less than the illustrated sixteen-slice system.

Figure 1:
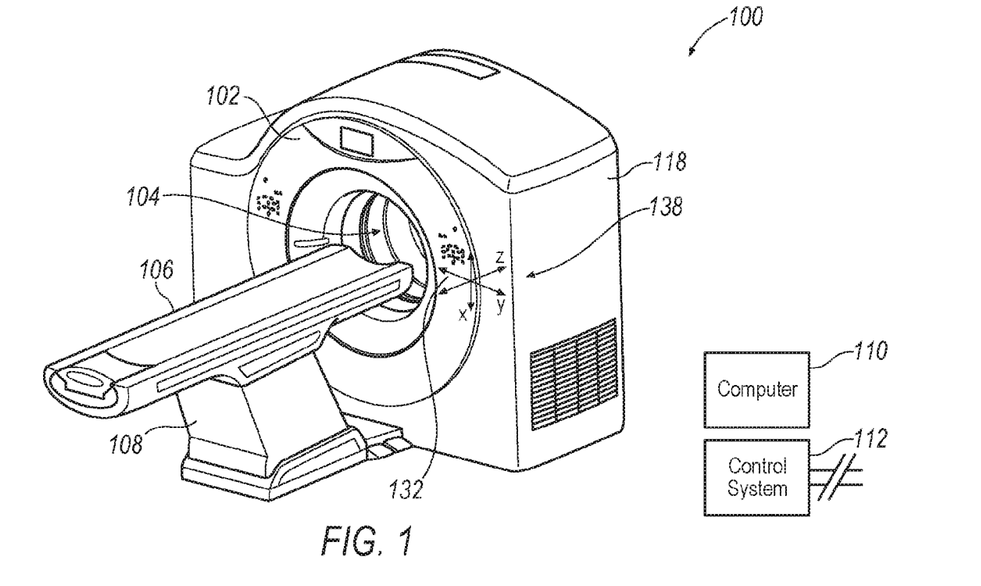
FIG. 1 is a perspective view of a CT imaging system.
Figure 2:
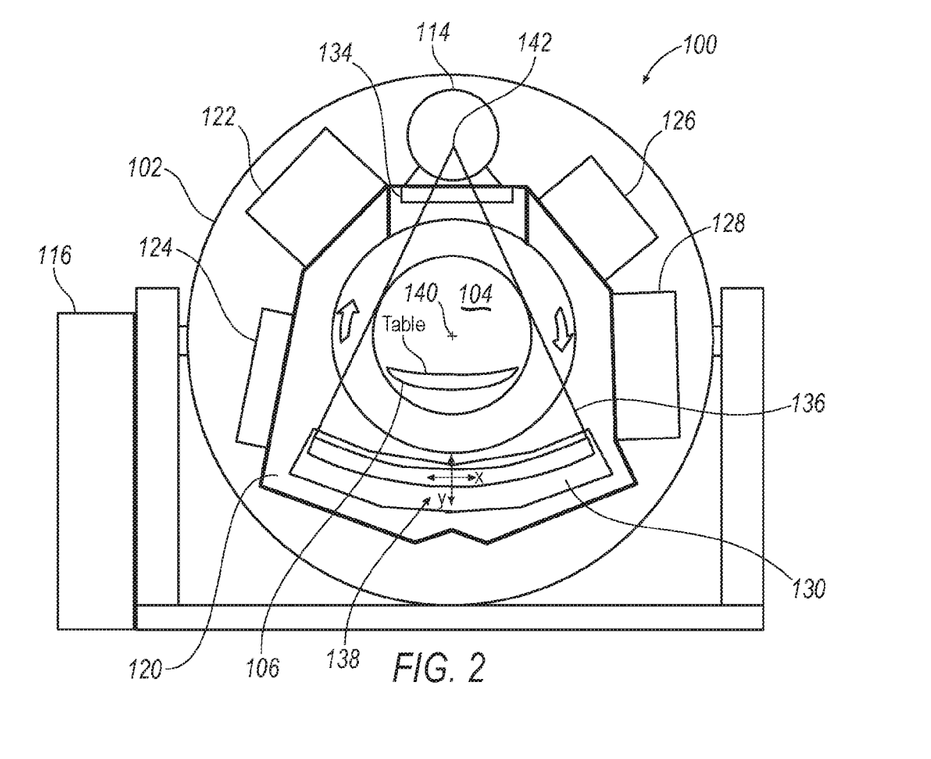
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate systems in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
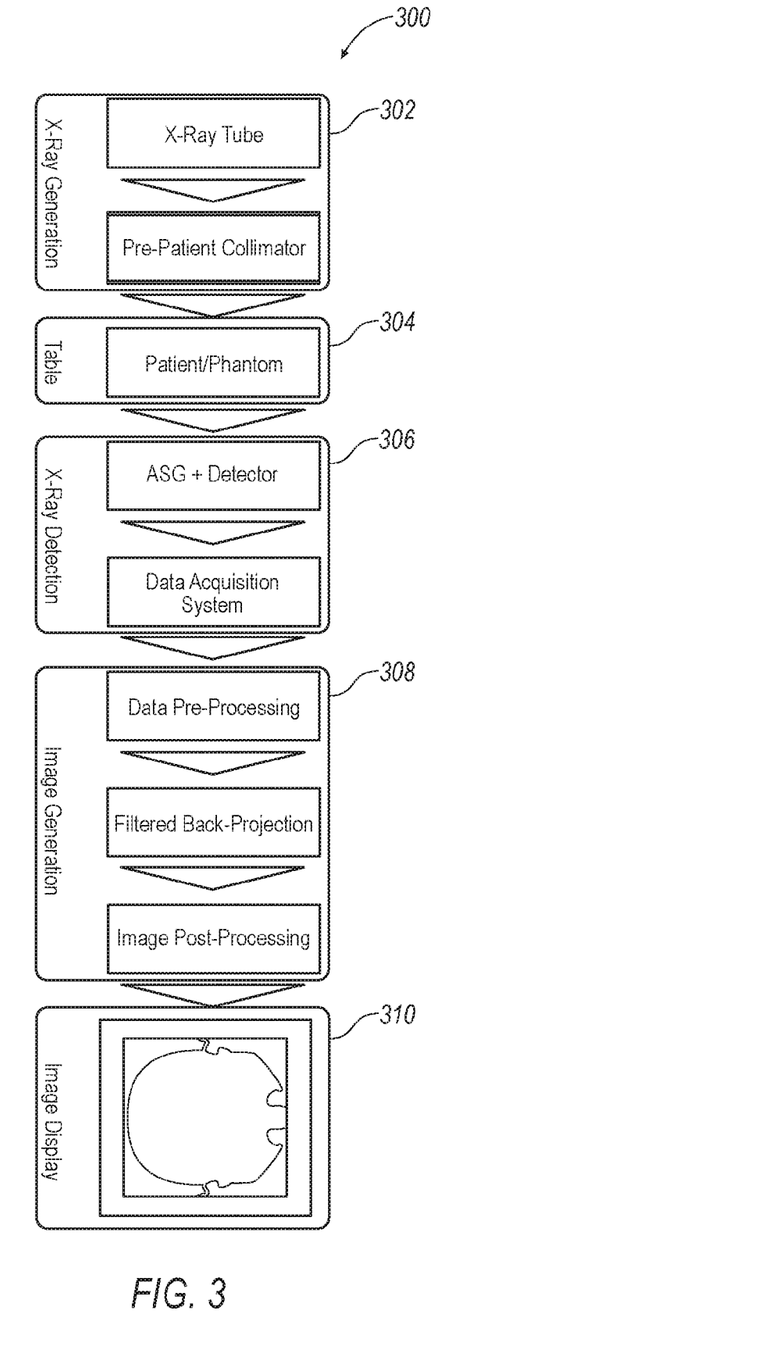
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which time table 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
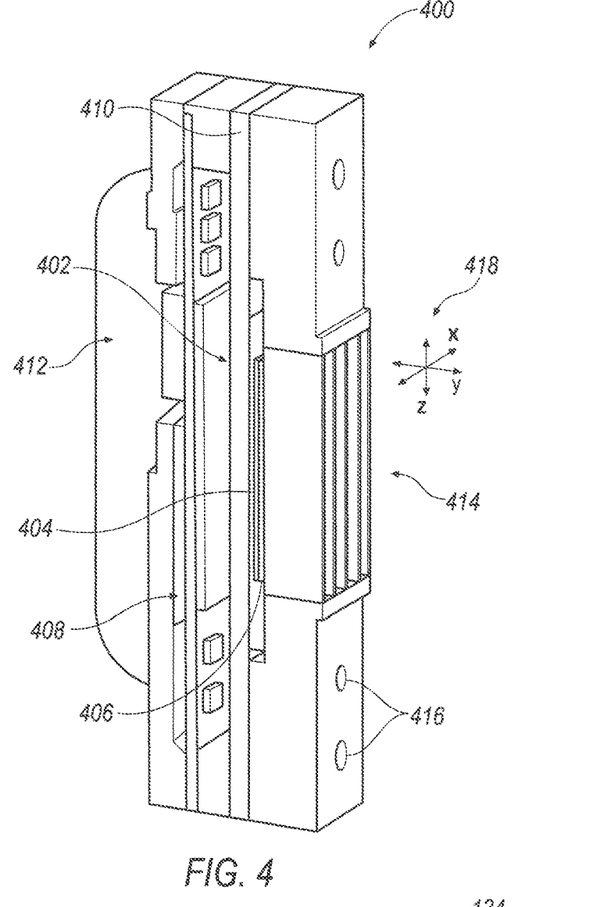
FIG. 4 is an example of a detector module.

FIG. 4 illustrates an exemplary detector module 400 that is one of a plurality of modules for use in detector assembly 130. A diode-scintillator array 402 includes a pixelated scintillator 404 positioned on a pixelated photodiode array 406. The photodiode array 402 may be either a front-lit or a back-lit type of photodiode. The diode-scintillator array 402 is positioned on an A/D board 408 that includes electronics components for signal processing, wherein analog electrical signals from diode-scintillator array 402 are digitized and then passed to DAS 124. Diode-scintillator array 402 is positioned on a base substrate 410 that may include a ceramic or other solid base material. A heat sink 412 is in thermal contact with A/D board 408 for providing enhanced cooling to the electronics located on A/D board 408. Detector module 400 also includes an anti-scatter grid (ASG) 414 that, in one embodiment, includes a plurality of plates (a few exemplary plates are shown) that are approximately parallel with a Y-Z plane of detector assembly 130. ASG 414, in the illustrated example, includes mount holes 416 which may be used for mounting module 400 to detector assembly 130 and aligning it therewith. FIG. 4 illustrates a triad 418 that illustrates corresponding X-Y-Z coordinates, as illustrated also in FIG. 1.

Figure 5:
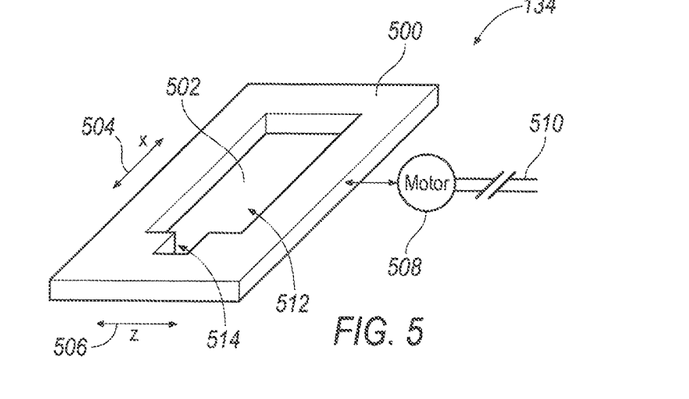
FIG. 5 illustrates a pre-patient collimator having an aperture that comprises two contiguous apertures for imaging and Z-motion calibration.

The CT system 100 of FIGS. 1 and 2 includes pre-patient collimator 134, rotatable gantry 102 having an opening 104 for receiving an object to be scanned, x-ray tube 114, and detector assembly 130. FIG. 5 illustrates a perspective view of aspects of pre-patient collimator 134, which includes a pre-patient collimator plate 500 having an opening or aperture 502 therein. Pre-patient collimator plate 500 extends in X-direction 504 and Z-direction 506, as illustrated therein, corresponding with triad 138. Pre-patient collimator 134 also includes a motor 508 that is coupled via control lines 510 to computer 110 and control system 112 of FIG. 1, to move pre-patient collimator plate 500 in Z-direction 506. Pre-patient collimator plate 500 includes a first aperture 512 and a second aperture 514. In the illustrated example, apertures 512 and 514 are contiguous with one another and, by one definition, constitute a single aperture. However, for the sake of clarity of discussion, apertures 512 and 514 are referred to as separate apertures, given that their separate sizes have relevance to the function of the disclosed method and device, although apertures 512 and 514 are contiguous with one another and are both part of opening or aperture 502. In one example, it is contemplated that apertures 512 and 514 may not be contiguous as a single aperture 502, but included as two separate apertures having a material therebetween. As will be further described, aperture 512 is used to pass x-rays used for imaging purposes, and aperture 512 is used to pass x-rays for calibration purposes and to better determine focal spot location 142 to improve image quality. As also will be further described, computer 110 is programmed to determine a focal spot location using energy derived from x-rays that fall upon a calibration area of pixels, and issue commands to a motor to adjust a position of the pre-patient collimator based on the determination.

Figure 6:
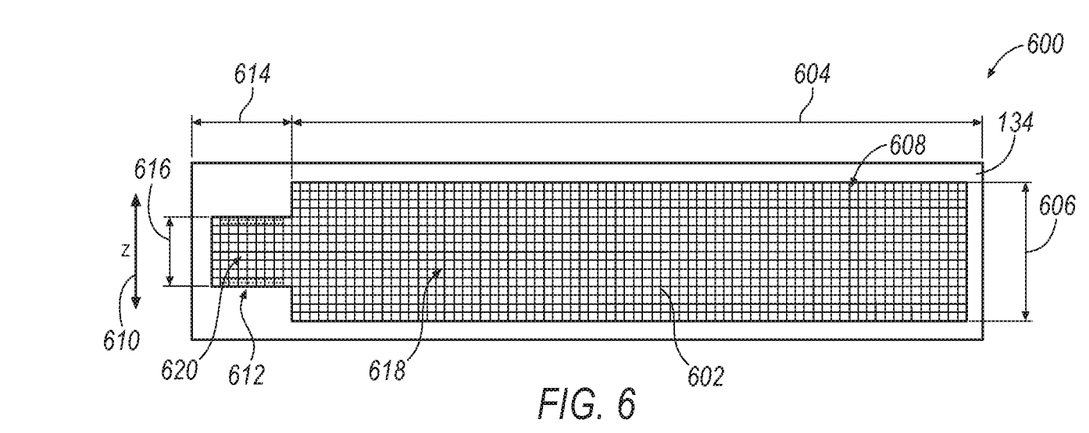
FIG. 6 illustrates an example of a view of a detector pixel arrays that are visible as seen from a perspective of a focal spot within x-ray tube.
Figure 7:
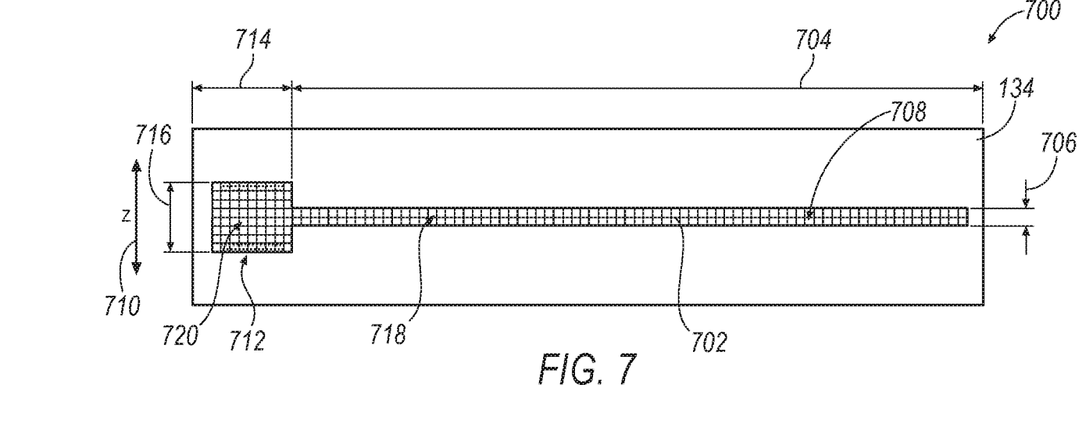
FIG. 7 illustrates an example of a view of a detector pixel arrays that are visible as seen from a perspective of a focal spot within x-ray tube.

FIGS. 6 and 7 illustrate views 600, 700 of respective detector pixel arrays 602, 702 that are visible as seen from a perspective of a focal spot within x-ray tube 114. Each view 600, 700 includes imaging detector pixels over a respective length 604, 704. It is contemplated that lengths 604, 704 correspond with a plurality of widths of modules 400 which, in one example, include 57 modules 400, each having 16 pixels in width. Thus, the illustrated grid of pixels over lengths 604, 704 does not illustrate a number of pixels corresponding to the example of 16 pixels wide in 57 modules, but is shown having a much larger scale of pixel sizes to simply illustrate the fact that pixels extend over lengths 604, 704 such that illustrative pixels can be seen in the figures. Each view 600, 700 also includes a width 606, 706 which are different from one another.

Views 600, 700, as mentioned, show detector pixel arrays 602, 702, which are actually the view of pixels in detector assembly 130 as seen in FIG. 2 and through per-patient collimator 134 therein. In one example, view 600 (FIG. 6) includes width 606, which is a width of an aperture, designated as aperture 502 in FIG. 5. As seen therein, aperture 502 is in pre-patient collimator plate 500, and is in the location of pre-patient collimator 134 as seen in FIG. 2, while the detector pixel array 602 is in detector assembly 130 as also seen in FIG. 2. Thus, width 606 of FIG. 6 illustrates a width of an aperture 608 that corresponds with, in one example, 16 pixels along a Z-direction 610. Pixel arrays 602, 702 are defined by a detector arc-length, such as along an arc length of detector assembly 130, and a plurality of pixels define an imaging Z-width such as width 606.

In another example, similarly, view 700 (FIG. 7) includes width 706 which is a width of an aperture, designated as aperture 502 in FIG. 5. Thus, width 706 of FIG. 7 illustrates a width of an aperture 708 that corresponds with, in another example, 2 pixels along a Z-direction 710.

Apertures 608, 708 correspond to imaging areas of pixels that are used to obtain imaging data for image reconstruction of an object. Apertures 608, 708 correspond with aperture 512 of FIG. 5 and, as mentioned, may have different widths to correspond with a different area of pixels that may be selected or available for imaging purposes. In one example (FIG. 7) two slices or pixel widths of data are available, and in another example (FIG. 6) 16 slices of data are available.

Opening or aperture 502 includes a second aperture 514 that is used to determine a focal spot location using energy derived from x-rays that fall upon a calibration area of pixels. In the illustrated examples of FIGS. 5 and 6, second apertures 612, 712 are provided for calibration. Apertures 612, 712 include corresponding lengths 614, 714. Apertures 612, 712 also include corresponding widths 616, 716 which, in the illustrated examples, each include 8 pixel widths.

Accordingly, pre-patient collimator 134 includes pre-patient collimator plate 500 that, in the example of FIG. 6, includes first aperture 608 having first length 604 and first width 606 such that x-rays pass therethrough to at least a portion of an imaging area 618 of pixel array 602. Pre-patient collimator plate 500 includes second aperture 612 having second length 614 and second width 610 such that x-rays pass therethrough to a calibration area 620 of pixel array 602. Thus, imaging area of pixels 618 and the calibration area of pixels 620 have different widths in a Z-direction of the CT scanning system.

In the example of FIG. 7, pre-patient collimator 134 includes pre-patient collimator plate 500 that includes first aperture 708 having first length 704 and first width 706 such that x-rays pass therethrough to at least a portion of an imaging area 718 of pixel array 702. Pre-patient collimator plate 500 includes second aperture 712 having second length 714 and second width 710 such that x-rays pass therethrough to a calibration area 720 of pixel array 702.

The calibration areas of pixels are used to track focal spot motion using pixels therein. For example, referring to FIG. 8, a calibration area of pixels 800 is shown that corresponds with calibration area of pixels 620 from FIG. 6. Calibration area of pixels 800 includes a first area of pixels 802 that are highlighted in FIG. 8 for illustration purposes, and a second area of pixels 804 at are on either side of first area of pixels 802. Second area of pixels 804 are for tracking focal spot motion such that the focal spot location of focal spot 142 is determined.

Figure 8:
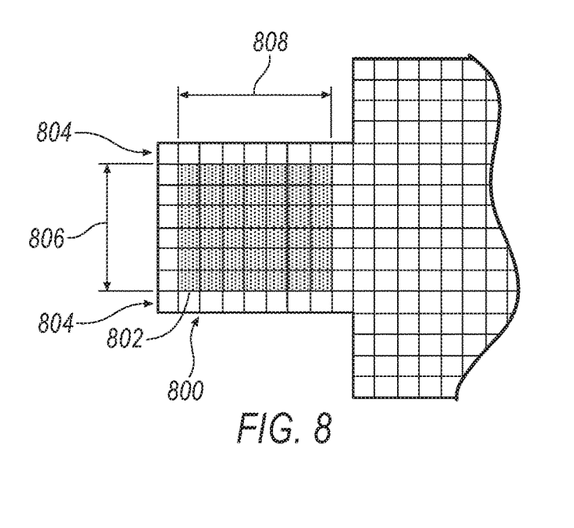
FIG. 8 illustrates a calibration area of pixels.

The first area of pixels 802 is one or more rows of central pixels as defined along the Z-direction, and the second area of pixels 804 that in the illustrated embodiment is outermost rows of pixels on either side of the first area of pixels 802 as defined along the Z-direction. Thus, in this example, area 802 is used for providing reference signals and area or rows 804 of pixels are used to provide feedback related to Z-motion of focal spot 142 to control the focal spot position and always maintain in a stable position or use the data to correct any gain variation induced by imperfection of the detector channel-channel or module-module responses.

Feedback for controlling the collimation aperture 502 is thereby provided by a few pixels 804 located at one extreme end of the collimator aperture 502 or slit. Pre-patient collimator plate 500 having aperture 502, comprised of two apertures 512, 514, is controlled by one motor. The aperture design is shown in FIG. 6 for a large aperture 608 and FIG. 7 for a small aperture 708. In these examples, the focal spot motion tracking aperture 800 is outside a field of view and is assigned a group of pixels 802 for reference channels and assigned a few pixels 804 for tracking the focal spot motion in Z-axis.

The partial exposure of pixels 804 will lead to a linear signal as a function of the focal spot motion. By monitoring the partial exposure of pixels 804, the focal spot can be tracked and compensated for any drift by, for example, re-adjusting grid voltages within a cathode driving the focal spot position, as is understood within the art. The focal spot position in Z is found to a monotonic function of the ratio of the signal from pixels 804 over a signal from the reference signals of pixels 802. It is contemplated that different numbers of pixels may be used for both the reference signals (pixels 802) and Z-motion pixels (804). That is, referring to FIG. 8, reference pixels 802 include a width 806 that includes 6 pixels therein, in an example, along a Z-direction. However, more or less pixels may be used for the reference signal pixels, as it is contemplated that in general although focal spot motion may occur, its effect is observed as partial exposure of pixels 804, while pixels 802 remain fully exposed. Thus, x-rays impinging on pixels 802 are generally unaffected by focal spot motion. Pixels 804, on the other hand, experience partial x-ray exposure that indeed changes with focal spot motion. Therefore, the signal in pixels 804 generally changes with focal spot motion or drift, while the signal in pixels 802 generally remains constant—independent of focal spot motion. Likewise, pixels 802 are shown over a calibration length 808 that includes the illustrated number of pixels, but it is contemplated that the length 808 may also include more or less pixels than shown.

Accordingly, based on the signal obtained and the ratio of signal from pixels, computer 110 is programmed to issue commands to motor 508 to adjust the position of the pre-patient collimator 500 in the Z-direction.

Figure 9:
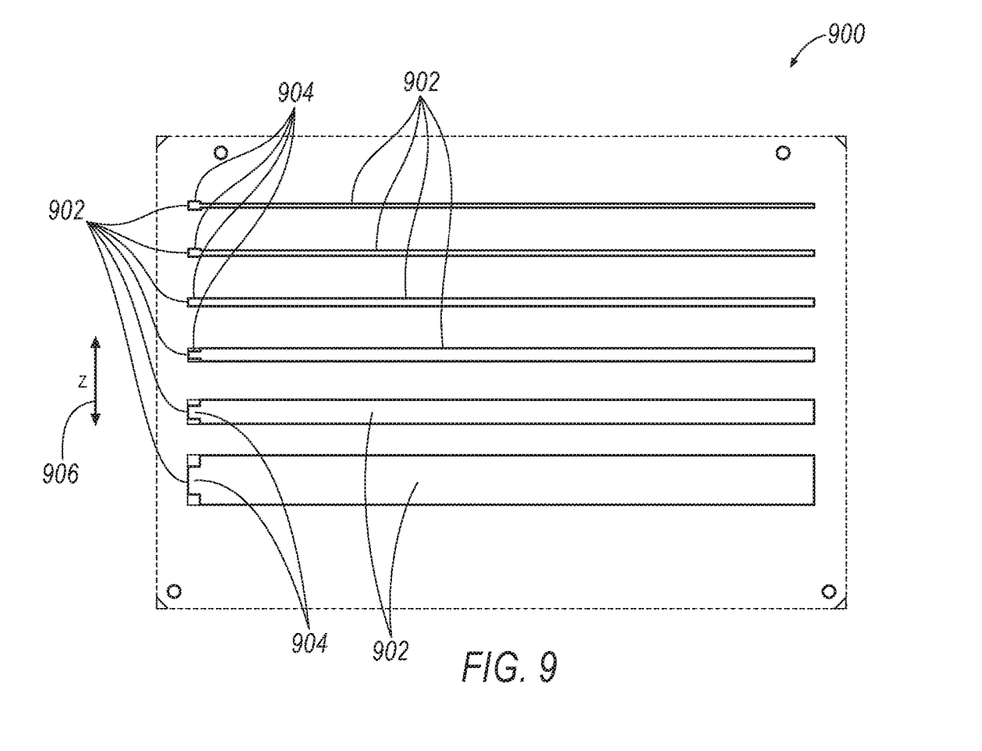
FIG. 9 illustrates a collimator plate having a plurality of apertures.

Referring to FIG. 9, a collimator plate 900 that includes a plurality of apertures 902, each of which includes an imaging aperture 902 and a Z-motion calibration aperture 904. Each aperture 902 includes a different width in a Z-direction 906. Z-motion calibration apertures 904 may be the same width in the Z-direction, or may be different in the Z-direction. Calibration apertures 904 may have different widths, which effectively results in a different amount of pixels used for reference channels. However, in each instance, calibration apertures 904 include a row of channels at the two Z-ends of the aperture that correspond generally with pixels 804 of FIG. 8. In such fashion, a reference signal may be determined from the central pixels that correspond generally with pixels 802 of FIG. 8, while a variable signal that varies with Z-position of the focal spot is received in pixels 804. Accordingly, the pre-patient collimator 900 in one example includes the plurality of pre-patient apertures 902 that are not contiguous with one another. Each aperture may thereby correspond with the aperture 502 as described above, having apertures 512, 514 combined. In one example, all calibration areas 902 may be of different widths in the Z-direction, while in another example all calibration areas 902 may be approximately the same (as illustrated in FIGS. 6 and 7).

Thus, the disclosure includes a method of CT imaging that includes passing x-rays through an opening in a pre-patient collimator, through an object, and to at least a portion of a detector, the detector including imaging pixels and calibration pixels, determining a focal spot location using energy derived from x-rays that fall upon the calibration area of pixels, and adjusting a position of the pre-patient collimator based on the determination.

An implementation of system 100 in an example comprises a plurality of components such as one or more of electronic components, hardware components, and/or computer software components. An exemplary component of an implementation of the system 100 employs and/or comprises a set and/or series of computer instructions written in or implemented with any of a number of programming languages, as will be appreciated by those skilled in the art.

An implementation of system 100 in an example employs one or more computer readable signal bearing media. A computer-readable signal-bearing medium in an example stores software, firmware and/or assembly language for performing one or more portions of one or more implementations. A computer-readable signal-bearing medium for an implementation of the system 100 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 100, for instance, an internal network, the Internet, a wireless network, and the like.

According to one embodiment, a CT scanning system includes a rotatable gantry having an opening for receiving an object to be scanned, an x-ray tube, and a detector comprising an imaging area of pixels and a calibration area of pixels. The system further includes a pre-patient collimator positioned between the x-ray tube and the detector having first and second apertures that pass x-rays respectively to at least a portion of the imaging area of pixels, and to the calibration area of pixels, a motor configured to move the pre-patient collimator, and a computer programmed to determine a focal spot location using energy derived from x-rays that fall upon the calibration area of pixels, and issue commands to a motor to adjust a position of the pre-patient collimator based on the determination.

According to another embodiment, a method of CT imaging includes passing x-rays through an opening in a pre-patient collimator, through an object, and to at least a portion of a detector, the detector including imaging pixels and calibration pixels, determining a focal spot location using energy derived from x-rays that fall upon the calibration area of pixels, and adjusting a position of the pre-patient collimator based on the determination.

A technical contribution for the disclosed method and apparatus is that it provides for a computer-implemented apparatus and method of determining a focal spot location using energy derived from x-rays that fall upon the calibration area of pixels, and issuing commands to a motor to adjust a position of the pre-patient collimator based on the determination.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:
1. A CT system comprising:
a rotatable gantry having an opening for receiving an object to be scanned;
an x-ray tube having a focal spot from which x-rays emit;

a detector comprising an imaging area of pixels and a calibration area of pixels;

a pre-patient collimator positioned between the x-ray tube and the detector having first and second apertures that pass x-rays respectively to at least a portion of the imaging area of pixels, and to the calibration area of pixels; and a computer programmed to:
determine a focal spot location in a Z-direction using energy derived from x-rays that fall upon the calibration area of pixels; and issue commands to adjust a Z-position of the focal spot based on the determined position of the focal spot from the x-rays that fall upon the calibration area of pixels, by adjusting a grid voltage within a cathode of the x-ray tube;

wherein the pre-patient collimator includes a plurality of apertures that are not contiguous with one another, each of which includes both imaging apertures and calibration apertures that are contiguous with one another, wherein the calibration apertures in each of the plurality of apertures have different widths from one another along the Z-direction and at least one of the calibration apertures is narrower than its corresponding imaging aperture, resulting in a different amount of pixels used for reference channels.

2. The CT system of claim 1, wherein the imaging area of pixels and the calibration area of pixels are contiguous with one another.

3. The CT system of claim 1, wherein the imaging area of pixels and the calibration area of pixels have different widths in the Z-direction of the CT scanning system.

4. The CT system of claim 1, wherein the calibration area of pixels includes:
a first area of pixels for providing reference signals; and
a second area of pixels for tracking focal spot motion such that the computer determines a location of the focal spot.

5. The CT system of claim 4, wherein:
the first area of pixels is one or more rows of central pixels as defined along the Z-direction; and
the second area of pixels are outermost rows of pixels on either side of the first area of pixels as defined along the Z-direction.

6. The CT system of claim 5, wherein the computer is programmed to determine the Z-position of the location of the focal spot using the energy derived from the x-rays that fall upon the second area of pixels.

7. The CT system of claim 1, wherein the computer is programmed to issue commands to a motor to adjust a position of the pre-patient collimator in the Z-direction, based on the determined position of the focal spot.

8. The CT system of claim 1, wherein the imaging apertures have widths in the Z-direction that are different from one another such that the x-rays that pass therethrough fall upon different sized portions of the imaging area of pixels.

9. A method of CT imaging, comprising:
passing x-rays through an opening in a pre-patient collimator, through an object, and to at least a portion of a detector, the detector including an imaging area of pixels and a calibration area of pixels;
determining a focal spot location using energy derived from x-rays that fall upon the calibration area of pixels; and
adjusting the focal spot location in a Z-direction by adjusting a grid voltage on a cathode, based on the determination of the focal spot location using the energy derived from x-rays that fall upon the calibration area of pixels;
wherein the pre-patient collimator includes a plurality of more than two apertures that are not contiguous with one another, each of which includes both imaging apertures and calibration apertures that are contiguous with one another, wherein the calibration apertures in each of the plurality of apertures have different widths from one another along the Z-direction and at least one of the calibration apertures is narrower than its corresponding imaging aperture, resulting in a different amount of pixels used for reference channels.

10. The method of claim 9, wherein passing the x-rays through the opening includes passing the x-rays to the imaging area of pixels and the calibration area of pixels that are contiguous with one another.

11. The method of claim 9, wherein the imaging area of pixels and the calibration area of pixels have different widths in the Z-direction of a CT scanning system.

12. The method of claim 9, wherein the calibration area of pixels includes:
a first area of pixels for providing reference signals; and
a second area of pixels for tracking focal spot motion such that a computer determines the focal spot location.

13. The method of claim 12, wherein:
the first area of pixels is one or more rows of central pixels as defined along the Z-direction; and
the second area of pixels are outermost rows of pixels on either side of the first area of pixels as defined along the Z-direction.

14. The method of claim 13, further comprising determining a Z-position of the focal spot location using the energy derived from the x-rays that fall upon the second area of pixels.

15. The method of claim 9, further comprising adjusting a position of the pre-patient collimator based on the determined focal spot location.

16. The method of claim 9, wherein the imaging apertures have widths in the Z-direction that are different from one another such that the x-rays that pass therethrough fall upon different sized portions of the imaging area of pixels.

* * * * *